US012465059B2

(12) United States Patent
K

(10) Patent No.: US 12,465,059 B2
(45) Date of Patent: Nov. 11, 2025

(54) CONCENTRATED FORMIC ACID COMPOSITION AND ITS USES THEREOF

(71) Applicant: Rithvik K, Tamil Nadu (IN)

(72) Inventor: Rithvik K, Tamil Nadu (IN)

(73) Assignee: Subha Krishnan, Tamilnadu (IN)

( * ) Notice: Subject to any disclaimer, the term of this patent is extended or adjusted under 35 U.S.C. 154(b) by 387 days.

(21) Appl. No.: 17/051,444

(22) PCT Filed: Aug. 9, 2018

(86) PCT No.: PCT/IN2018/000043
§ 371 (c)(1),
(2) Date: Oct. 29, 2020

(87) PCT Pub. No.: WO2019/239419
PCT Pub. Date: Dec. 19, 2019

(65) Prior Publication Data

US 2021/0251260 A1 Aug. 19, 2021

(30) Foreign Application Priority Data

Jun. 14, 2018 (IN) ............................. 201841022237

(51) Int. Cl.

| | |
|---|---|
| ***C11D 3/20*** | (2006.01) |
| ***A01N 37/02*** | (2006.01) |
| ***A23L 3/3508*** | (2006.01) |
| ***A61Q 19/00*** | (2006.01) |
| *A61K 8/36* | (2006.01) |
| *A61K 8/60* | (2006.01) |
| *A61Q 11/00* | (2006.01) |

(52) U.S. Cl.
CPC ............ *A23L 3/3508* (2013.01); *A01N 37/02* (2013.01); *A61Q 19/00* (2013.01); *A61K 8/36* (2013.01); *A61K 8/602* (2013.01); *A61Q 11/00* (2013.01)

(58) Field of Classification Search
CPC ......... C11D 1/667; C11D 3/042; C11D 3/201; C11D 3/2065; C11D 3/43; C11D 7/265; C11D 7/3218; C11D 7/50; C11D 7/5022
See application file for complete search history.

(56) References Cited

U.S. PATENT DOCUMENTS

| | | | | |
|---|---|---|---|---|
| 4,199,469 | A * | 4/1980 | Walzer | C11D 3/43 510/253 |
| 4,629,574 | A * | 12/1986 | Nuesslein | C11D 1/62 510/525 |
| 5,286,404 | A * | 2/1994 | Eriksen | C11D 3/38618 510/393 |
| 5,489,397 | A * | 2/1996 | Bainbridge | C11D 3/3765 510/475 |
| 7,144,846 | B2 * | 12/2006 | Keller | C11D 3/2075 510/132 |
| 2007/0123444 | A1 * | 5/2007 | Wahl | C11D 17/046 510/439 |
| 2008/0004200 | A1 * | 1/2008 | Boutique | C11D 3/33 510/393 |
| 2008/0004201 | A1 * | 1/2008 | Boutique | C11D 3/38663 510/393 |
| 2009/0270304 | A1 * | 10/2009 | Cermenati | C11D 3/2075 510/420 |
| 2009/0320212 | A1 * | 12/2009 | Brown | C11D 17/045 510/329 |
| 2010/0154823 | A1 * | 6/2010 | Cermenati | C11D 3/30 510/109 |
| 2014/0249068 | A1 * | 9/2014 | Murphy | C11D 3/30 510/346 |
| 2016/0151527 | A1 * | 6/2016 | Holland | C11D 1/60 544/2 |
| 2017/0101604 | A1 * | 4/2017 | Miracle | C11D 3/42 |
| 2017/0145345 | A1 * | 5/2017 | Gonzales | C11D 3/2068 |

* cited by examiner

*Primary Examiner* — Charles I Boyer

(57) ABSTRACT

The present invention is related to Methanoic acid composition and it's uses thereof.
The Methanoic acid composition helps in reducing the germicidal load and finds utility in dental hygiene, Cosmetics, detergents, soaps, skin cleansers, surface cleaners, water sanitizers, animal feed, processed food, poultry farms, poultry hatcheries and the pharmaceutical arena.

3 Claims, No Drawings

CONCENTRATED FORMIC ACID COMPOSITION AND ITS USES THEREOF

The present invention relates to a Novel and Inventive composition comprising Methanoic acid and other ingredients selected from beta—D-Fructofuranosyl-(2-1)-alpha—D-glucopyranoside, (2R,3S,4R,5R)-2,3,4,5,6-Pentahydroxyhexanal, (3S,4R,5R)-1,3,4,5,6-Pentahydroxyhexan-2-one, beta-D-galactopyranosyl-(1→4)-D-glucose, (2S,3R,4R,5R)-Hexane-1,2,3,4,5,6-hexol, Propane-1,2,3-triol, Propane-1,2-diol, Polyoxyethylene (20) sorbitan monooleate, Poly Oxyl 40 Hydrogenated Castor Oil, Ethanoic acid, Phenylmethanol, Propan-2-ol, poly(oxyethylene) with a Molecular weight of around 400, 2-Aminoethan-1-ol, 2,2'-Iminodiethanol, 2,2',2"-Nitrilotri(ethan-1-ol), (9Z)-Octadec-9-enoic acid, Octadecanoic acid, Hexadecanoic acid and Dihydrogen monoxide or a combination thereof for reducing the microbial/germ load.

Methanoic acid is an example of one of the Safest Cost Effective Antimicrobial as it is most easily digested/metabolized and finally breaks down to Carbon Dioxide & water after killing the germs. The present invention relates to such compositions which reduces bacterial and or germicidal load.

Unlike EVERY other Disinfectant/Antimicrobial which are completely alien to a body upon intake and which accumulate and/or cause toxic harm by itself or by breaking down to toxic products, Methanoic acid is completely safe and harmless and is widely used as a preservative.

Methanoic acid is a natural ingredient found in apples, strawberries, raspberries and honey.

Methanoic acid has been tested and found to be very safe with a toxicity of just 1.7 times more than that of the safest essential chemical ever known namely Sodium Chloride ie Common Salt.

The LD 50 of Methanoic acid in Rat is 1100 mg/Kg (oral) while the LD 50 of Sodium Chloride in Rat is 3000 mg/Kg (oral).

Amongst all the Organic Acids known, Methanoic acid is the most powerful.

Methanoic acid is 10 times (1000%) stronger than the second best strongest straight chain Organic Acid ie Acetic Acid.

The mode of action of the working of Methanoic acid is explained below.

Upon intake by the bacteria/microbe, Methanoic acid dissociates into it's $H^+$ ions. The bacteria/microbe consume a huge amount of energy to throw out the $H^+$ ions and kill itself in this process. Notwithstanding the above good features, Methanoic acid is not very widely used in several varied applications on account of a few of the listed drawbacks.

The Drawbacks are

It's Acidity:

Commercially available Methanoic acid is extremely acidic having a pH of less than 1.

Most precisely, the pH of commercially available Methanoic acid is 0.68 ie it is as much acidic as Concentrated Hydrochloric acid.

The Blenders/Mixers and Packing Equipments or any object coming in contact will corrode heavily if commercially available Methanoic acid is used as an ingredient.

Pungent Smell:

Commercially available Methanoic acid has a very Pungent Smell making it very difficult to use it on a regular basis, even if well equipped exhaust/ventilation systems are provided.

The inventor of the present application has surprisingly identified that when Methanoic acid is specially admixed with the following ingredients, individually or in a combination thereof, it helps to overcome the above mentioned drawbacks.

To Specifically Point Out

Acidity:

The very low pH of Methanoic acid is suitably altered.

The Methanoic acid composition of the present invention has a pH of around 5 to around 9.

Smell and Taste:

The Pungent smell is overcome. The Methanoic acid composition of the present invention has no Smell and loses it's acidic acrid taste.

The Methanoic acid composition of the present invention wherein the Methanoic acid ranges from 0.45% to 95.15% to the total weight of the composition and the said other ingredient or a combination of the said ingredients is/are taken from 4.85% to 99.55% to the total weight of the composition.

The present invention further relates to a Dental Hygiene composition comprising the composition of the present invention.

The present invention further relates to a Cosmetic composition comprising the composition of the present invention.

The present invention further relates to a Detergent composition comprising the composition of the present invention.

The present invention further relates to a Soap composition comprising the composition of the present invention.

The present invention further relates to a Food product comprising the composition of the present invention.

The present invention further relates to a Food product coated with the composition of the present invention.

The present invention further relates to an Animal feed composition comprising the composition of the present invention.

The present invention further relates to a Cleansing composition comprising the composition of the present invention.

The present invention further relates to a Water sanitation composition comprising the composition of the present invention.

The present invention further relates to a Surface cleaning composition comprising the composition of the present invention.

The present invention further relates to a Pharmaceutical composition comprising the composition of the present invention.

The present invention further relates to a composition used to reduce the germicidal load on the skin comprising the composition of the present invention.

The present invention further relates to a process for the preparation of the composition of the present invention wherein the said composition is obtained by mixing Methanoic acid with other ingredients selected from beta—D-Fructofuranosyl-(2→1)-alpha—D-glucopyranoside, (2R,3S,4R,5R)-2,3,4,5,6-Pentahydroxyhexanal, (3S,4R,5R)-1,3,4,5,6-Pentahydroxyhexan-2-one, beta-D-galactopyranosyl-(1→4)-D-glucose, (2S,3R,4R,5R)-Hexane-1,2,3,4,5,6-hexol, Propane-1,2,3-triol, Propane-1,2-diol, Polyoxyethylene (20) sorbitan monooleate, Poly Oxyl 40 Hydrogenated Castor Oil, Ethanoic acid, Phenylmethanol, Propan-2-ol, poly(oxyethylene) with a Molecular weight of around 400, 2-Aminoethan-1-ol, 2,2'-Iminodiethanol, 2,2',2"-Nitrilotri(ethan-1-ol), (9Z)-Octadec-9-enoic acid, Octadecanoic acid, Hexadecanoic acid and Dihydrogen monoxide or a combination thereof to result in a product having a pH between 5 to 9.

Though the present invention refers to and provides to a list of ingredients other than Methanoic acid it is to be understood that the 'other ingredients' does not exclude such other ingredients other than beta—D-Fructofuranosyl-(2-1)-alpha-D-glucopyranoside, (2R,3S,4R,5R)-2,3,4,5,6-Pentahydroxyhexanal, (3S,4R,5R)-1,3,4,5,6-Pentahydroxyhexan-2-one, beta-D-galactopyranosyl-(1→4)-D-glucose, (2S,3R,4R,5R)-Hexane-1,2,3,4,5,6-hexol, Propane-1,2,3-triol, Propane-1,2-diol, Polyoxyethylene (20) sorbitan monooleate, Poly Oxyl 40 Hydrogenated Castor Oil, Ethanoic acid, Phenylmethanol, Propan-2-ol, poly(oxyethylene) with a Molecular weight of around 400, 2-Aminoethan-1-ol, 2,2'-Iminodiethanol, 2,2',2"-Nitrilotri(ethan-1-ol), (9Z)-Octadec-9-enoic acid, Octadecanoic acid, Hexadecanoic acid and Dihydrogen monoxide that affects and changes the biological action of the improvised Methanoic acid metabolism on the lines of the present invention.

The Methanoic acid composition of the present invention is suited for multifaceted applications including use in dental hygiene, Cosmetics, detergents, soaps, skin cleansers, surface cleaners, water sanitizers, animal feed, processed food, poultry farms, poultry hatcheries, pharmaceutical arena etc.

EXAMPLE 1

Aim: To compare the bactericidal activity of Methanoic acid composition solution along with other commercial disinfectants available in the market on the Pathogenic culture *Pseudomonas aeruginosa.*

Scope:

To determine the bactericidal activity of disinfectant solutions by streak plate method as per the procedure prescribed in the Pharmacopeia on the Pathogenic culture *Pseudomonas aeruginosa.*

Media Used:

Tryptone soya agar/Nutrient agar.

Incubation Period:

Incubate for 48 Hours at 30-35° C.

Samples Preparation:

Methanoic acid composition is processed by mixing 59 grams of Commercially available Methanoic acid of 85% concentration with 10 grams of beta—D-Fructofuranosyl-(2→1)-alpha—D-glucopyranoside and 31 grams of Dihydrogen monoxide. The other Commercial Disinfectants [represented herein by their Trade Names] are purchased directly from the market.

The process adopted is by Trial and identification method.

A known quantity of the Disinfectant is made up to 100 ml in a Sterile Standard Flask with water separately.

Preparation of Media & Inoculation of Culture:

4 g of tryptone soya agar is dissolved in 100 ml of above dilute solutions separately and kept in a water bath for few minute for the agar to dissolve.

Petri plate, inoculation loop & agar were autoclaved at 121° C. for 15 minutes for sterilization.

The Sterile agar was then poured into the petri plate for solidification.

After solidification the pathogenic culture namely *Pseudomonas aeruginosa* was streaked in the agar.

The Petri plates were then incubated in the incubator for 2 days in 30-35° C.

Result:

The quantity of Disinfectant Required to ensure NIL GROWTH of the pathogen *Pseudomonas aeruginosa* in the Petri Plate is presented below.

1.3 gm of Methanoic Acid composition of Example 1 was sufficient to ensure NIL GROWTH of *Pseudomonas aeruginosa* in the Petri Plate.

8 gms of Savlon was required to ensure NIL GROWTH of *Pseudomonas aeruginosa* in the Petri Plate implying that the Methionic Acid composition presented in the present application is 6 times more potent than that of Savlon.

10 gms of Lizol was required to ensure NIL GROWTH of *Pseudomonas aeruginosa* in the Petri Plate implying that the Methionic Acid composition presented in the present application is 7.6 times more potent than that of Lizol.

11 gms of Dettol was required to ensure NIL GROWTH of *Pseudomonas aeruginosa* in the Petri Plate implying that the Methionic Acid composition presented in the present application is 8.4 times more potent than that of Dettol.

26 gms of Domex was required to ensure NIL GROWTH of *Pseudomonas aeruginosa* in the Petri Plate implying that the Methionic Acid composition presented in the present application is 20 times more potent than that of Domex.

28 gms of Harpic was required to ensure NIL GROWTH of *Pseudomonas aeruginosa* in the Petri Plate implying that the Methionic Acid composition presented in the present application is 21.5 times more potent than that of Harpic.

EXAMPLE 2

Aim: To compare the bactericidal activity of Methanoic acid composition solution along with other commercial disinfectants available in the market on the Pathogenic culture *Staphylococcus aureus.*

Scope:

To determine the bactericidal activity of disinfectant solutions by streak plate method as per the procedure prescribed in the Pharmacopeia on the Pathogenic culture *Staphylococcus aureus.*

Media Used:

Tryptone soya agar/Nutrient agar.

Incubation Period:

Incubate for 48 Hours at 30-35° C.

Samples Preparation:

Methanoic acid composition is processed by mixing 59 grams of Commercially available Methanoic acid of 85% concentration with 10 grams of (2R,3S,4R,5R)-2,3,4,5,6-Pentahydroxyhexanal and 31 grams of Dihydrogen monoxide. The other Commercial Disinfectants are purchased directly from the market.

The process adopted is by Trial and identification method.

A known quantity of the Disinfectant is made up to 100 ml in a Sterile Standard Flask with water separately.

Preparation of Media & Inoculation of Culture:

4 g of tryptone soya agar is dissolved in 100 ml of above dilute solutions separately and kept in a water bath for few minute for the agar to dissolve.

Petri plate, inoculation loop & agar were autoclaved at 121° C. for 15 minutes for sterilization.

The Sterile agar was then poured into the petri plate for solidification.

After solidification the pathogenic culture namely *Staphylococcus aureus* was streaked in the agar.

The Petri plates were then incubated in the incubator for 2 days in 30-35° C.

Result:

The quantity of Disinfectant Required to ensure NIL GROWTH of the pathogen *Staphylococcus aureus* in the Petri Plate is presented below.

1.2 gm of Methanoic Acid composition was sufficient to ensure NIL GROWTH of *Staphylococcus aureus* in the Petri Plate.

9 gms of Savlon was required to ensure NIL GROWTH of *Staphylococcus aureus* in the Petri Plate implying that the Methionic Acid composition presented in the present application is 7.5 times more potent than that of Savlon.

10 gms of Lizol was required to ensure NIL GROWTH of *Staphylococcus aureus* in the Petri Plate implying that the Methionic Acid composition presented in the present application is 8.3 times more potent than that of Lizol.

11 gms of Dettol was required to ensure NIL GROWTH of *Staphylococcus aureus* in the Petri Plate implying that the Methionic Acid composition presented in the present application is 9.1 times more potent than that of Dettol.

27 gms of Domex was required to ensure NIL GROWTH of *Staphylococcus aureus* in the Petri Plate implying that the Methionic Acid composition presented in the present application is 22.5 times more potent than that of Domex.

29 gms of Harpic was required to ensure NIL GROWTH of *Staphylococcus aureus* in the Petri Plate implying that the Methionic Acid composition presented in the present application is 24.1 times more potent than that of Harpic.

EXAMPLE 3

Aim: To compare the bactericidal activity of Methanoic acid composition solution along with other commercial disinfectants available in the market on the Pathogenic culture *Escherichia coli.*

Scope:

To determine the bactericidal activity of disinfectant solutions by streak plate method as per the procedure prescribed in the Pharmacopeia on the Pathogenic culture *Escherichia coli.*

Media Used:

Tryptone soya agar/Nutrient agar.

Incubation Period:

Incubate for 48 Hours at 30-35° C.

Samples Preparation:

Methanoic acid composition is processed by mixing 59 grams of Commercially available Methanoic acid of 85% concentration with 10 grams of (3S,4R,5R)-1,3,4,5,6-Pentahydroxyhexan-2-one and 31 grams of Dihydrogen monoxide. The other Commercial Disinfectants are purchased directly from the market.

The process adopted is by Trial and identification method.

A known quantity of the Disinfectant is made up to 100 ml in a Sterile Standard Flask with water separately.

Preparation of Media & Inoculation of Culture:

4 g of tryptone soya agar is dissolved in 100 ml of above dilute solutions separately and kept in a water bath for few minute for the agar to dissolve.

Petri plate, inoculation loop & agar were autoclaved at 121° C. for 15 minutes for sterilization.

The Sterile agar was then poured into the petri plate for solidification.

After solidification the pathogenic culture namely *Escherichia coli* was streaked in the agar.

The Petri plates were then incubated in the incubator for 2 days in 30-35° C.

Result:

The quantity of Disinfectant required to ensure NIL GROWTH of the pathogen *Escherichia coli* in the Petri Plate is presented below.

1.3 gm of Methanoic Acid composition was sufficient to ensure NIL GROWTH of *Escherichia coli* in the Petri Plate.

9 gms of Savlon was required to ensure NIL GROWTH of *Escherichia coli* in the Petri Plate implying that the Methionic Acid composition presented in the present application is 6.9 times more potent than that of Savlon.

14 gms of Lizol was required to ensure NIL GROWTH of *Escherichia coli* in the Petri Plate implying that the Methionic Acid composition presented in the present application is 10.7 times more potent than that of Lizol.

18 gms of Dettol was required to ensure NIL GROWTH of *Escherichia coli* in the Petri Plate implying that the Methionic Acid composition presented in the present application is 13.8 times more potent than that of Dettol.

27 gms of Domex was required to ensure NIL GROWTH of *Escherichia coli* in the Petri Plate implying that the Methionic Acid composition presented in the present application is 20.7 times more potent than that of Domex.

29 gms of Harpic was required to ensure NIL GROWTH of *Escherichia coli* in the Petri Plate implying that the Methionic Acid composition presented in the present application is 22.3 times more potent than that of Harpic.

EXAMPLE 4

Aim: To compare the bactericidal activity of Methanoic acid composition solution along with other commercial disinfectants available in the market on the Pathogenic culture *Salmonella abony.*

Scope:

To determine the bactericidal activity of disinfectant solutions by streak plate method as per the procedure prescribed in the Pharmacopeia on the Pathogenic culture *Salmonella abony.*

Media Used:

Tryptone soya agar/Nutrient agar.

Incubation Period:

Incubate for 48 Hours at 30-35° C.

Samples Preparation:

Methanoic acid composition is processed by mixing 59 grams of Commercially available Methanoic acid of 85% concentration with 10 grams of beta-D-galactopyranosyl-(1→4)-D-glucose and 31 grams of Dihydrogen monoxide. The other Commercial Disinfectants are purchased directly from the market.

The process adopted is by Trial and identification method.

A known quantity of the Disinfectant is made up to 100 ml in a Sterile Standard Flask with water separately.

Preparation of Media & Inoculation of Culture:

4 g of tryptone soya agar is dissolved in 100 ml of above dilute solutions separately and kept in a water bath for few minute for the agar to dissolve.

Petri plate, inoculation loop & agar were autoclaved at 121° C. for 15 minutes for sterilization.

The Sterile agar was then poured into the petri plate for solidification.

After solidification the pathogenic culture namely *Salmonella abony* was streaked in the agar.

The Petri plates were then incubated in the incubator for 2 days in 30-35° C.

Result:

The quantity of Disinfectant Required to ensure NIL GROWTH of the pathogen *Salmonella abony* in the Petri Plate is presented below.

1.4 gm of Methanoic Acid composition was sufficient to ensure NIL GROWTH of *Salmonella abony* in the Petri Plate.

8 gms of Savlon was required to ensure NIL GROWTH of *Salmonella abony* in the Petri Plate implying that the Methionic Acid composition presented in the present application is 5.7 times more potent than that of Savlon.

10 gms of Lizol was required to ensure NIL GROWTH of *Salmonella abony* in the Petri Plate implying that the Methionic Acid composition presented in the present application is 7.1 times more potent than that of Lizol.

10 gms of Dettol was required to ensure NIL GROWTH of *Salmonella abony* in the Petri Plate implying that the Methionic Acid composition presented in the present application is 7.1 times more potent than that of Dettol.

28 gms of Domex was required to ensure NIL GROWTH of *Salmonella abony* in the Petri Plate implying that the Methionic Acid composition presented in the present application is 20 times more potent than that of Domex.

30 gms of Harpic was required to ensure NIL GROWTH of *Salmonella abony* in the Petri Plate implying that the Methionic Acid composition presented in the present application is 21.4 times more potent than that of Harpic.

EXAMPLE 5

The samples of the present composition as indentified in below table were prepared and each sample is identified with an alphabet.

TABLE 1

| Ingredient | Sample A Weight % to the total weight of the composition | Sample B Weight % to the total weight of the composition | Sample C Weight % to the total weight of the composition | Sample D Weight % to the total weight of the composition | Sample E Weight % to the total weight of the composition | Sample F Weight % to the total weight of the composition | Sample G Weight % to the total weight of the composition | Sample H Weight % to the total weight of the composition |
|---|---|---|---|---|---|---|---|---|
| Methanoic acid with 85% purity | 95.00 | 82.75 | 76.57 | 55.65 | 49.95 | 32.80 | 22.77 | 15.45 |
| beta-D-Fructofuranosyl-(2→1)-alpha-D-glucopyranoside, | 0.32 | 1.25 | 2.02 | NIL | 4.55 | 3.45 | 8.98 | 7.45 |
| (2R,3S,4R,5R)-2,3,4,5,6-Pentahydroxyhexanal, | 0.28 | 1.50 | NIL | 4.35 | 5.25 | 4.00 | 7.55 | 9.12 |
| (3S,4R,5R)-1,3,4,5,6-Pentahydroxyhexan-2-one | 0.58 | 2.15 | 2.80 | NIL | 7.25 | 4.57 | 6.23 | 6.66 |
| beta-D-galactopyranosyl-(1→4)-D-glucose | 0.44 | 2.11 | 0.68 | NIL | 4.98 | 3.20 | 8.34 | 6.77 |
| (2S,3R,4R,5R)-Hexane-1,2,3,4,5,6-hexol | 0.38 | 1.63 | 2.25 | NIL | 4.02 | 4.78 | 6.13 | 2.00 |
| Propane-1,2,3-triol | 0.25 | 0.75 | NIL | 3.25 | 1.78 | 2.66 | NIL | 2.00 |
| Propane-1,2-diol | 0.25 | 1.06 | NIL | NIL | 0.58 | NIL | 4.88 | 2.00 |
| Polyoxyethylene (20) sorbitan monooleate, | 0.10 | 1.00 | 1.25 | 3.77 | 1.64 | 7.34 | 4.48 | 2.00 |
| Poly Oxyl 40 Hydrogenated Castor Oil | 0.20 | 0.65 | 2.00 | NIL | 2.00 | 2.80 | 2.64 | 2.00 |
| Ethanoic acid | 0.15 | 0.58 | 1.72 | NIL | 2.25 | 2.06 | 3.62 | 3.00 |
| Phenylmethanol, | 0.10 | 0.47 | 0.5 | 2.98 | 0.75 | 1.58 | 4.15 | NIL |
| Propan-2-ol, | 0.25 | 0.67 | 0.5 | 1.55 | 0.75 | 2.25 | NIL | 3.18 |
| poly(oxyethylene) | 0.25 | NIL | 1.78 | NIL | 2.25 | 1.58 | NIL | 1.59 |
| 2-Aminoethan-1-ol, | 0.20 | NIL | 2.00 | NIL | 1.58 | 2.27 | NIL | 2.98 |
| 2,2'-Iminodiethanol | 0.20 | 0.50 | 0.25 | 4.55 | 2.28 | 3.02 | 5.41 | 2.25 |

TABLE 1-continued

| Ingredient | Sample A Weight % to the total weight of the composition | Sample B Weight % to the total weight of the composition | Sample C Weight % to the total weight of the composition | Sample D Weight % to the total weight of the composition | Sample E Weight % to the total weight of the composition | Sample F Weight % to the total weight of the composition | Sample G Weight % to the total weight of the composition | Sample H Weight % to the total weight of the composition |
|---|---|---|---|---|---|---|---|---|
| 2,2',2''-Nitrilotri(ethan-1-ol), | 0.25 | 0.73 | 1.00 | NIL | 2.25 | NIL | 4.82 | 0.70 |
| (9Z)-Octadec-9-enoic acid | 0.10 | NIL | 1.25 | 3.90 | 0.09 | NIL | 4.44 | NIL |
| Octadecanoic acid | 0.10 | 0.40 | 0.25 | 1.25 | 0.40 | 2.78 | 2.25 | 2.25 |
| Hexadecanoic acid | 0.20 | 0.80 | 0.03 | 1.25 | 0.40 | 3.34 | 0.31 | 4.05 |
| Dihydrogen monoxide | 0.40 | 1.00 | 3.15 | 17.5 | 5.00 | 15.52 | 3.00 | 24.55 |

The following Table-2 lists out the quantity of known disinfectants to ensure NIL GROWTH upon the pathogens tested as indicated therein.

TABLE 2

| Example Number | Quantum of known disinfectant required to obtain NIL GROWTH | Pathogen tested upon |
|---|---|---|
| 1 | a) 1.3 gm of Methanoic acid composition<br>b) 8 g of SAVLON<br>c) 10 g of LIZOL<br>d) 11 g of DETTOL<br>e) 26 g of DOMEX<br>f) 28 g of HARPIC | *Psedomonas aeruginosa* |
| 2 | a) 1.2 gms of Methanoic acid composition<br>b) 9 g of SAVLON<br>c) 10 g of LIZOL<br>d) 11 g of DETTOL<br>e) 27 g of DOMEX<br>f) 29 g of HARPIC | *Staphylococcus aureus* |
| 3 | a) 1.3 gms of Methanoic acid composition<br>b) 9 g of SAVLON<br>c) 14 g of LIZOL<br>d) 18 g of DETTOL<br>e) 27 g of DOMEX<br>f) 29 g of HARPIC | *Escherichia coli* |
| 4 | a) 1.4 gms of Methanoic acid composition<br>b) 8 g of SAVLON<br>c) 10 g of LIZOL<br>d) 10 g of DETTOL<br>e) 28 g of DOMEX<br>f) 30 g of HARPIC | *Salmonella abony* |

The following table exemplifies the effect of the compositions as identified by Sample A to Sample H of Table 1 over the pathogens as referred in Table 2.

TABLE 3

| PATHOGEN TESTED UPON | Quantum of known disinfectant required to obtain NIL GROWTH | Quantum of composition of the invention required to obtain NIL GROWTH | REMARKS [Higher Effectiveness] |
|---|---|---|---|
| *Psedomonas aeruginosa* | a) 8 g of SAVLON | 0.8 gms of the Methanoic | Methanoic acid composition as |

TABLE 3-continued

| PATHOGEN TESTED UPON | Quantum of known disinfectant required to obtain NIL GROWTH | Quantum of composition of the invention required to obtain NIL GROWTH | REMARKS [Higher Effectiveness] |
|---|---|---|---|
| | b) 10 g of LIZOL<br>c) 11 g of DETTOL<br>d) 26 g of DOMEX<br>e) 28 g of HARPIC | composition as presented by the alphabet "A" in Table 1 above was sufficient to ensure Nil Growth | presented by the alphabet "A" in Table 1 above is thus<br>a) 10 times as effective as SAVLON<br>b) 12.5 times as effective as LIZOL<br>c) 13.75 times as effective as DETTOL<br>d) 32.5 times as effective as DOMEX<br>e) 35 times as effective as HARPIC |
| *Staphylococcus aureus* | a) 9 g of SAVLON<br>b) 10 g of LIZOL<br>c) 11 g of DETTOL<br>d) 27 g of DOMEX<br>e) 29 g of HARPIC | 0.8 gms of the Methanoic composition as presented by the alphabet "B" in Table 1 above was sufficient to ensure Nil Growth | Methanoic acid composition as presented by the alphabet "B" in Table 1 above is thus<br>a) 11.25 times as effective as SAVLON<br>b) 12.5 times as effective as LIZOL<br>c) 13.75 times as effective as DETTOL<br>d) 33.75 times as effective as DOMEX<br>e) 38.6 times as effective as HARPIC |
| *Escherichia coli* | a) 9 g of SAVLON<br>b) 14 g of LIZOL<br>c) 18 g of DETTOL<br>d) 27 g of DOMEX | 1 gm of the Methanoic composition as presented by the alphabet "C" in Table 1 above was sufficient to | Methanoic acid composition as presented by the alphabet "C" in Table 1 above is thus<br>a) 9 times as effective as SAVLON |

TABLE 3-continued

| PATHOGEN TESTED UPON | Quantum of known disinfectant required to obtain NIL GROWTH | Quantum of composition of the invention required to obtain NIL GROWTH | REMARKS [Higher Effectiveness] |
|---|---|---|---|
| | e) 29 g of HARPIC | ensure Nil Growth | b) 14 times as effective as LIZOL c) 18 times as effective as DETTOL d) 27 times as effective as DOMEX e) 29 times as effective as HARPIC |
| *Salmonella abony* | a) 8 g of SAVLON b) 10 g of LIZOL c) 10 g of DETTOL d) 28 g of DOMEX e) 30 g of HARPIC | 1.5 gms of the Methanoic composition as presented by the alphabet "D" in Table 1 above was sufficient to ensure Nil Growth | Methanoic acid composition as presented by the alphabet "D" in Table 1 above is thus a) 5.3 times as effective as SAVLON b) 6.6 times as effective as LIZOL c) 6.6 times as effective as DETTOL d) 18.6 times as effective as DOMEX e) 20 times as effective as HARPIC |
| *Psedomonas aeruginosa* | a) 8 g of SAVLON b) 10 g of LIZOL c) 11 g of DETTOL d) 26 g of DOMEX e) 28 g of HARPIC | 1.6 gms of the Methanoic acid composition as presented by the alphabet "E" in Table 1 above was sufficient to ensure Nil Growth | Methanoic acid composition as presented by the alphabet "E" in Table 1 above is thus a) 5 times as effective as SAVLON b) 6.25 times as effective as LIZOL c) 6.8 times as effective as DETTOL d) 16.25 times as effective as DOMEX e) 17.5 times as effective as HARPIC |
| *Staphylococcus aureus* | a) 9 g of SAVLON b) 10 g of LIZOL c) 11 g of DETTOL d) 27 g of DOMEX e) 29 g of HARPIC | 2.2 gms of the Methanoic acid composition as presented by the alphabet "F" in Table 1 above was sufficient to ensure Nil Growth | Methanoic acid composition as presented by the alphabet "F" in Table 1 above is thus a) 4 times as effective as SAVLON b) 4.5 times as effective as LIZOL c) 5 times as effective as DETTOL d) 12.2 times as effective as DOMEX e) 13.1 times as effective as HARPIC |

TABLE 3-continued

| PATHOGEN TESTED UPON | Quantum of known disinfectant required to obtain NIL GROWTH | Quantum of composition of the invention required to obtain NIL GROWTH | REMARKS [Higher Effectiveness] |
|---|---|---|---|
| *Escherichia coli* | a) 9 g of SAVLON b) 14 g of LIZOL c) 18 g of DETTOL d) 27 g of DOMEX e) 29 g of HARPIC | 3.4 gms of the Methanoic acid composition as presented by the alphabet "G" in Table 1 above was sufficient to ensure Nil Growth | Methanoic acid composition as presented by the alphabet "G" in Table 1 above is thus a) 2.6 times as effective as SAVLON b) 4.1 times as effective as LIZOL c) 5.2 times as effective as DETTOL d) 7.9 times as effective as DOMEX e) 8.5 times as effective as HARPIC |
| *Salmonella abony* | a) 8 g of SAVLON b) 10 g of LIZOL c) 10 g of DETTOL d) 28 g of DOMEX e) 30 g of HARPIC | 5.4 gms of the Methanoic acid composition as presented by the alphabet "H" in Table 1 above was sufficient to ensure Nil Growth | Methanoic acid composition as presented by the alphabet "H" in Table 1 above is thus a) 1.4 times as effective as SAVLON b) 1.8 times as effective as LIZOL c) 1.8 times as effective as DETTOL d) 5.1 times as effective as DOMEX e) 5.5 times as effective as HARPIC |

It may be noted that the composition of the invention can be used without admixing with any other composition. It may further be noted that the composition of the invention can be admixed with any other known composition to obtain the desired combined effects of the composition mixtures. It may further be noted that in such mixing compositions the mixing ratio does not place much role because the skilled person in the artisan will be capable of doing so.

What is claimed is:

1. A formic acid composition comprising formic acid ranging from 15.45 to 95 percent to the total weight of the composition and a compound selected from the group consisting of Sucrose, Glucose, Fructose, Lactose, Mannitol, Glycerin, Propylene glycol, Polyoxyethylene (20) sorbitan monooleate, Polyoxyl 40 Hydrogenated Castor Oil, Acetic Acid, Benzyl alcohol, Isopropyl alcohol, Polyethylene glycol, Ethanolamine, Diethanolamine, Triethanolamine, Oleic acid, Stearic acid and Palmitic acid or a combination thereof and balancing amount of water wherein the said product has a pH between 5 to 9 to enable reduction in microbial/germs load.

2. A process for the preparation of the formic acid composition as claimed in claim 1 wherein the said composition is obtained by mixing formic acid ranging from 15.45 to 95 percent to the total weight of the composition with a compound selected from the group consisting of Sucrose Glucose, Fructose, Lactose, Mannitol, Glycerin, Propylene glycol, Polyoxyethylene (20) sorbitan monooleate, Polyoxyl 40 Hydrogenated Castor Oil, Acetic Acid, Benzyl alcohol, Isopropyl alcohol, Polyethylene glycol, Ethanolamine, Diethanolamine, Triethanolamine, Oleic acid, Stearic acid and Palmitic acid or a combination thereof and balancing amount of water is added to result in a product having a pH between 5 to 9.

3. A process to assess the effectiveness of formic acid composition of claim 1 in reducing the microbe/germ load in a given substrate comprising the steps of;

a) Preparing formic acid composition of by mixing formic acid ranging from 15.45 to 95 percent to the total weight of the composition with the compound selected from Sucrose, Glucose, Fructose, Lactose, Mannitol, Glycerin, Propylene glycol, Polyoxyethylene (20) sorbitan monooleate, Polyoxyl 40 Hydrogenated Castor Oil, Acetic Acid, Benzyl alcohol, Isopropyl alcohol, Polyethylene glycol, Ethanolamine, Diethanolamine, Triethanolamine, Oleic acid, Stearic acid and Palmitic acid or a combination thereof and balancing amount of water to make 100% total weight of the composition;

b) Preparing media and inoculation culture by dissolving 4 gram of tryptone soya sugar in 100 ml of the composition of step (a) and keep it aside till agar to dissolve;

c) sterilizing petri plate, inoculation loop and agar by autoclaving at 121° C. for 15 minutes;

d) solidifying agar by pouring agar onto the petri plate;

e) streaking microorganisms or germs in the agar;

f) incubating the petri plate in an incubator for 2 days in 30-35° C.

g) repeating the steps (b) to (f) with any other known disinfectant h) assessing and comparing the amount of formic acid composition of step (a) with the amount of any known disinfectant to achieve the nil growth of microorganisms/germs.

* * * * *